US00PP28304P2

(12) United States Plant Patent
Misato

(10) Patent No.: US PP28,304 P2
(45) Date of Patent: Aug. 15, 2017

(54) ***SENECIO* PLANT NAMED 'SUNSENEYONA'**

(50) Latin Name: *Senecio cruentus*
Varietal Denomination: Sunseneyona

(71) Applicant: Tomoya Misato, Shiga (JP)

(72) Inventor: Tomoya Misato, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 14/999,695

(22) Filed: Jun. 16, 2016

(51) Int. Cl.
*A01H 5/02* (2006.01)

(52) U.S. Cl.
USPC ..... Plt./480

(58) Field of Classification Search
USPC ..... Plt./480
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Senecio* plant named 'Sunseneyona', characterized by its upright and uniformly mounded plant habit; vigorous growth habit; freely branching habit; freely flowering habit; and daisy-type inflorescences with ray florets that are dark red purple in color becoming gradually lighter in color towards the base.

1 Drawing Sheet

Botanical designation: *Senecio cruentus.*
Cultivar denomination: 'SUNSENEYONA'.

BACKGROUND OF THE INVENTION

The present invention relates to a new and distinct cultivar of *Senecio* plant, botanically known as *Senecio cruentus*, and hereinafter referred to by the name 'Sunseneyona'.

The new *Senecio* plant is a product of a planned breeding program conducted by the Inventor in Higashiomi, Shiga, Japan. The objective of the breeding program is to create new upright and uniformly mounding *Senecio* plants with a freely-branching habit and numerous attractive inflorescences.

The new *Senecio* plant originated from a cross pollination conducted by the Inventor in March, 2010 of a proprietary selection of *Senecio cruentus* identified as code number 09-123, not patented, as the female, or seed, parent with a proprietary selection of *Senecio cruentus* identified as code number 09-83, not patented, as the male, or pollen, parent. The new *Senecio* plant was discovered and selected by the Inventor as a single flowering plant within the progeny of the stated cross-pollination in a controlled greenhouse environment in Higashiomi, Shiga, Japan in February, 2011.

Asexual reproduction of the new *Senecio* plant by terminal cuttings in a controlled greenhouse environment in Higashiomi, Shiga, Japan since October, 2011 has shown that the unique features of this new *Senecio* plant are stable and reproduced true to type in successive generations.

SUMMARY OF THE INVENTION

Plants of the new *Senecio* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Sunseneyona'. These characteristics in combination distinguish 'Sunseneyona' as a new and distinct *Senecio* plant:

1. Upright and uniformly mounded plant habit.
2. Vigorous growth habit.
3. Freely branching habit.
4. Freely flowering habit.
5. Daisy-type inflorescences with ray florets that are dark red purple in color becoming gradually lighter in color towards the base.

Plants of the new *Senecio* can be compared to plants of the female parent selection. Plants of the new *Senecio* differ from plants of the female parent selection in the following characteristics:

1. Plants of the new *Senecio* have broader ray florets than plants of the female parent selection.
2. Plants of the new *Senecio* and the female parent selection differ in ray floret color as plants of the female parent selection have ray florets that are blue in color becoming gradually lighter towards the base.

Plants of the new *Senecio* can be compared to plants of the male parent selection. Plants of the new *Senecio* differ from plants of the male parent selection in the following characteristics:

1. Plants of the new *Senecio* have broader ray florets than plants of the male parent selection.
2. Plants of the new *Senecio* and the male parent selection differ in ray floret color as plants of the male parent selection have violet and rose-colored ray florets.

Plants of the new *Senecio* can also be compared to plants of *Senecio cruentus*×*Senecio heritieri* 'Sunsenere', disclosed in U.S. Plant Pat. No. 12,162. In side-by-side comparisons, plants of the new *Senecio* differ from plants of 'Sunsenere' in the following characteristics:

1. Plants of the new *Senecio* have longer internodes than plants of 'Sunsenere'.
2. Plants of the new *Senecio* have smaller leaves with shorter petioles than plants of 'Sunsenere'.
3. Plants of the new *Senecio* have larger inflorescences than plants of 'Sunsenere'.

4. Plants of the new *Senecio* and 'Sunsenere' differ in ray floret color as plants of 'Sunsenere' have more purple-colored ray florets.
5. Ray floret apices of plants of the new *Senecio* are more rounded than and not as acute as ray floret apices of plants of 'Sunsenere'.
6. Plants of the new *Senecio* have shorter peduncles than plants of 'Sunsenere'.

BRIEF DESCRIPTION OF THE PHOTOGRAPHS

The accompanying photographs illustrate the overall appearance of the new *Senecio* plant showing the colors as true as it is reasonably possible to obtain in colored reproductions of this type. Colors in the photographs may differ slightly from the color values cited in the detailed botanical description which accurately describe the colors of the new *Senecio* plant.

The photograph at the top of the sheet is a side perspective view of a typical flowering plant of 'Sunseneyona' grown in a container.

The photograph at the bottom of the sheet is a close-up view of a typical flowering plant of 'Sunseneyona'.

DETAILED BOTANICAL DESCRIPTION

The aforementioned photographs, following observations and measurements describe plants grown during the winter in 15-cm containers in an outdoor nursery in Higashiomi, Shiga, Japan and under cultural practices typical of commercial *Senecio* production. During the production of the plants, day temperatures averaged 10° C. and night temperatures averaged 5° C. Measurements and numerical values represent averages for typical flowering plants. Plants were five months old when the photographs and description were taken. In the following description, color references are made to The Royal Horticultural Society Colour Chart, 2007 Edition, except where general terms of ordinary dictionary significance are used.

Botanical classification: *Senecio cruentus* 'Sunseneyona'.

Parentage:

*Female, or seed, parent*.—Proprietary selection of *Senecio cruentus* identified as code number 09-123, not patented.

*Male, or pollen, parent*.—Proprietary selection of *Senecio cruentus* identified as code number 09-83, not patented.

Propagation:

*Type*.—Terminal vegetative cuttings.

*Time to initiate roots, summer and winter*.—About one week at temperatures about 18° C. to 20° C.

*Time to produce a rooted young plant, summer and winter*.—About four weeks at temperatures about 18° C. to 20° C.

*Root description*.—Fine, fibrous; typically white in color, actual color of the roots is dependent on substrate composition, water quality, fertilizer type and formulation, substrate temperature and physiological age of roots.

*Rooting habit*.—Freely branching.

Plant description:

*Plant form and growth habit*.—Upright and uniformly mounded plant habit; daisy-type inflorescences positioned above the foliar plane; freely branching habit; vigorous growth habit; freely branching habit with about eight primary lateral branches with numerous secondary branches.

*Plant height*.—About 22 cm.

*Plant diameter*.—About 29 cm.

*Lateral branches*.—Length: About 18 cm. Diameter: About 3.5 mm. Internode length: About 2.3 cm. Strength: Strong. Aspect: Upright to outwardly. Texture: Densely pubescent. Color: Close to 144A.

*Leaf description*.—Arrangement: Alternate, simple. Length: About 5.6 cm. Width: About 6.3 cm. Shape: Cordate. Apex: Acute. Base: Cordate. Margin: Shallowly serrate. Texture and luster, upper surface: Sparsely pubescent; matte. Texture and luster, lower surface: Densely pubescent; rough; matte. Venation pattern: Pinnate; reticulate. Color: Developing leaves, upper surface: Close to 137C. Developing leaves, lower surface: Close to 191B. Fully expanded leaves, upper surface: Close to N137C; venation, close to 145B. Fully expanded leaves, lower surface: Close to 191A; venation, close to 147C. Leaf petioles: Length: About 4.7 cm. Diameter: About 2.3 mm. Texture, upper and lower surfaces: Pubescent. Color, upper and lower surfaces: Close to 146C.

Inflorescence description:

*Appearance*.—Daisy-type inflorescences with lanceolate-shaped ray florets; inflorescences arising from upper leaf axils and positioned above the foliar plane on strong peduncles; disc and ray florets developing acropetally on a capitulum; inflorescences face mostly upright to slightly outwardly; freely flowering habit with about 41 inflorescences per plant.

*Fragrance*.—None detected.

*Natural flowering season*.—Plants of the new *Senecio* begin flowering about 22 weeks after planting; plants flower continuously from winter to late spring in Japan.

*Inflorescence longevity*.—Inflorescences last about two weeks on the plant; inflorescences persistent.

*Inflorescence buds*.—Height: About 2.1 cm. Diameter: About 8.5 mm. Shape: Globose. Color: Close to 59A.

*Inflorescence size*.—Diameter: About 7.1 cm. Depth (height): About 1.5 cm. Disc diameter: About 1.3 cm.

*Receptacles*.—Diameter: About 6.7 mm. Height: About 1.5 mm. Color: Close to 144C.

*Ray florets*.—Length: About 3 cm. Width: About 8.3 mm. Shape: Lanceolate. Apex: Rounded. Base: Obtuse. Margin: Entire. Aspect: Initially upright, then horizontal; flat. Texture, upper and lower surfaces: Smooth, glabrous. Number of ray florets per inflorescence: About 13 in a single whorl. Color: When opening, upper surface: Close to 61A. When opening, lower surface: Longitudinally streaked with close to 64A and 75D. Fully opened, upper surface: Towards the apex, close to 71A; towards the base, close to 71C to 71D; with development, distal color becoming closer to 70A and proximal color becoming closer to N74C. Fully opened, lower surface: Longitudinally streaked with close to 72B and 73D.

*Disc florets*.—Shape: Tubular; apex dentate, five-pointed. Length: About 8.1 mm. Diameter, at apex: About 2.5 mm. Diameter, at base: About 1 mm.

Number of disc floret per inflorescence: About 114. Color, immature: Close to 59A. Color, mature: Close to 71A.

*Phyllaries*.—Quantity per inflorescence: About 13 in a single whorl. Length: About 7 mm. Width: About 2 mm. Shape: Lanceolate. Apex: Narrowly acute. Base: Fused. Margin: Entire. Texture, upper and lower surfaces: Smooth, glabrous. Color, upper surface: Close to 138A; towards the apex, close to 138B. Color, lower surface: Close to 137C; towards the apex, close to 138C; at the apex, close to N77A.

*Peduncles*.—Length: About 3.2 cm. Diameter: About 1.5 mm. Strength: Strong. Aspect: Upright to outwardly. Texture: Smooth, glabrous. Color: Close to 138A.

*Reproductive organs*.—Androecium: Present on disc florets only. Filament length: About 0.8 mm. Filament color: Close to NN155C. Anther size: About 2.2 mm by 0.3 mm. Anther shape: Narrowly ellipsoidal. Anther color: Close to 165A. Pollen amount: Moderate. Pollen color: Close to 15A. Gynoecium: Present on both ray and disc florets. Pistil length: About 5.8 mm. Stigma shape: Bi-parted. Stigma color: Close to 187A. Style color: Towards the apex, close to 59D; mid-section, close to 182C; towards the base, close to 145D. Ovary color: Close to 145D.

*Seeds and fruits*.—Seed and fruit development have not been observed on plants of the new *Senecio*.

Disease & pest resistance: Plants of the new *Senecio* have not been observed to be resistant to pathogens and pests common to *Senecio* plants.

Temperature tolerance: Plants of the new *Senecio* have been observed to tolerate temperatures ranging from about 0° C. to about 30° C.

It is claimed:

1. A new and distinct *Senecio* plant named 'Sunseneyona' as illustrated and described.

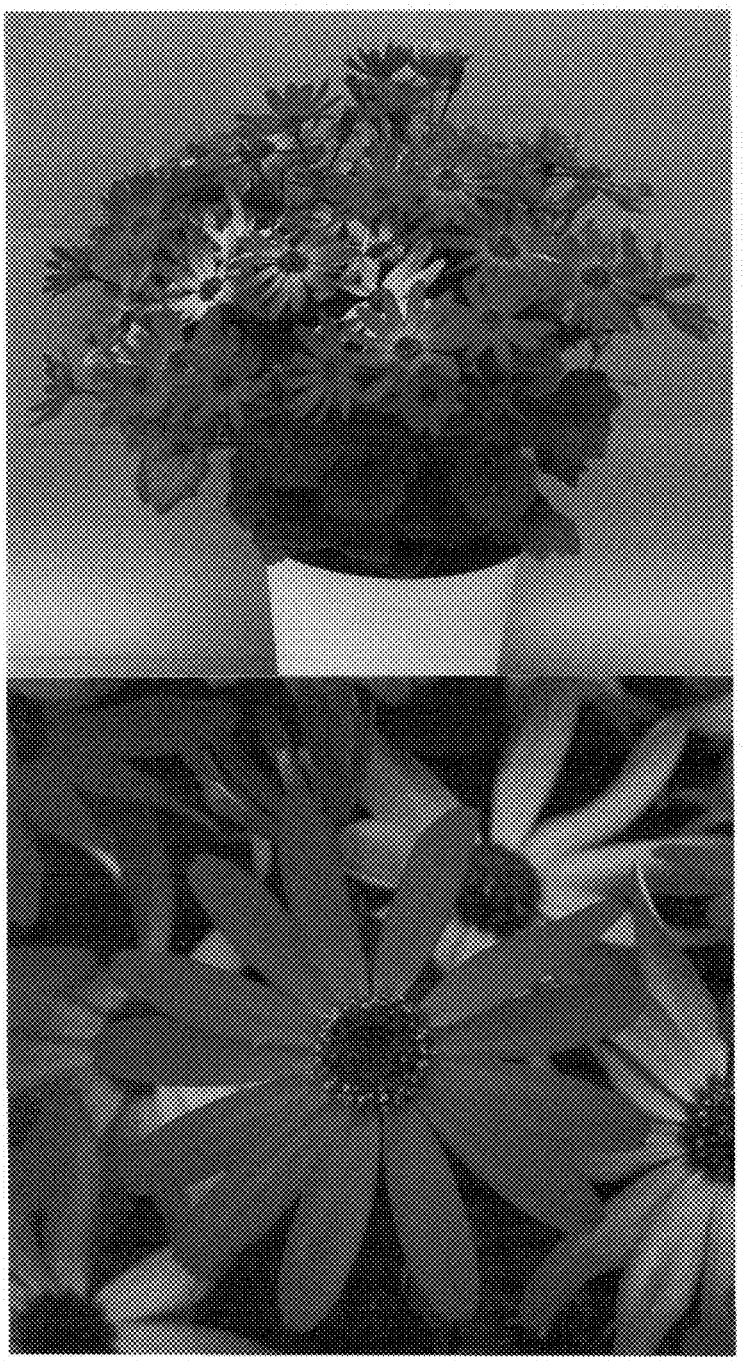

* * * * *